United States Patent [19]

Carruth

[11] Patent Number: Plant 7,588

[45] Date of Patent: Jul. 16, 1991

[54] HYBRID MINIATURE ROSE PLANT NAMED "WEKSYBIL"

[75] Inventor: Thomas F. Carruth, Altadena, Calif.

[73] Assignee: Weeks Wholesale Rose Grower, Inc., Upland, Calif.

[21] Appl. No.: 496,818

[22] Filed: Mar. 20, 1990

[51] Int. Cl.[5] ..... A01H 5/00

[52] U.S. Cl. ..... Plt./7

[58] Field of Search ..... Plt. 7, 14

[56] References Cited

U.S. PATENT DOCUMENTS

P.P. 3,601 8/1974 Moore ..... Plt. 7

P.P. 6,714 4/1989 Christensen et al. ..... Plt. 14

*Primary Examiner*—James R. Feyrer

*Attorney, Agent, or Firm*—Christie, Parker & Hale

[57] ABSTRACT

A new hybrid miniature rose for garden decoration. The plant is of a dwarf, bushy, upright growth habit and may be distinguished from other presently available rose cultivars by the following combination of characteristics: coloration of deep pink to red with a white eyezone and reverse, large pointed buds and well-formed blooms, long lasting flowers, abundant glossy foliage of good disease resistance, and a vigorous productive plant.

1 Drawing Sheet

BACKGROUND OF THE INVENTION

This invention relates to a new and distinct variety of hybrid miniature rose. The plant is of a dwarf, bushy, upright growth habit, suitable for growing outdoor, and may be cultivated for garden decoration. It was bred by Thomas F. Carruth in Canoga Park, Calif., and has as its seed parent, the rose known as "Arobipy" and as its pollen parent the rose known as "Magic Carrousel" (U.S. Plant Pat. No. 3,601). The varietal denomination of the new variety is "Weksybil".

SUMMARY OF THE INVENTION

The new variety may be distinguished from other presently available commercial rose cultivars by the following combination of characteristics: coloration of deep pink with a white eyezone and reverse essentially as described and illustrated herein, large pointed buds and well-formed blooms, long lasting flowers, abundant glossy foliage of good disease resistance, and a vigorous productive plant. Weksybil may be propagated by cuttings, budding, grafting, layering and tissue culture. I have asexually reproduced the plant 'Weksybil' by rooting cuttings taken therefrom.

Asexual propagation of the new variety as performed in Kern County, Calif., shows that the foregoing and other distinguishing characteristics come true to form and are established and transmitted through succeeding propagations.

The new rose may be distinguished from its seed parent, Arobipy by the following combination of characteristics: whereas Arobipy is a hybrid tea, the new cultivar is a miniature. Whereas the seed parent has a predominantly white coloration, Weksybil has a distinctly different flower coloration of deep pink with a white eyezone and reverse essentially as described and illustrated herein. The new variety has virtually no fragrance, whereas the seed parent possesses a pronounced fragrance.

The new variety may be distinguished from its pollen parent, "Magic Carrousel" by the following combination of characteristics: whereas the pollen parent bears white flowers with a fine red edging, Weksybil bears flowers with a significantly broader edging of deep pink essentially as described and illustrated herein. Magic Carrousel bears flowers with a diameter of about 4 cm., whereas the new seedling bears significantly larger flowers of between 5 to 6 cm. diameter.

BRIEF DESCRIPTION OF THE ILLUSTRATION

The accompanying photograph illustrates the plant in color and shows the flowering thereof from bud to full bloom, depicted in color as nearly correct as it is possible to make in an illustration of this character. Throughout this description, color names and values are based upon the Colour Chart of The Royal Horticultural Society of London, England, except where common terms of color definition are employed.

DESCRIPTION OF THE NEW VARIETY

The following description pertains to rose plants of the new cultivar grown outdoor in February, 1990, in Kern County, and in Upland, Calif. and is believed to apply to plants of the variety grown elsewhere in similar conditions of soil and climate.

FLOWER

The new variety bears its flowers usually singly, sometimes two or three per stem. Flowers are borne in regular rounded clusters on strong short to medium length stems for this class. Outdoor, the plant blooms very freely and nearly continuously during the growing season. The flowers have no perceptible fragrance.

BUD

The peduncle is of average to long length for the class, of average to heavy caliper, and usually stiff. It is moderately smooth with very few stipitate glands and numerous hairs. Peduncle color is near to between Yellow-Green 146A and Green 137B with a moderate overlay of near Greyed-Orange 166B.

Before the calyx breaks, the bud is of large size for the class, of medium length, and pointed to ovoid in shape. The surface of the bud bears some foliaceous parts extending beyond the tip of the bud equal to ½ or more of its length. Bud color is near to between Yellow-Green 146A and Green 137B.

The inner surface of the sepals is lined with fine wooly tomentum; sepal margins are lined with few stipitate glands and many hairs.

As the first petals open, the bud is moderately large for the class, of medium length, and moderately pointed to ovoid in form. The color of the outside surface of the newly opened petals has a broad base of near White 155A that gradually suffuses to a edging of near to between Red-Purple 60B to D and Red 53B. The color of the inside surface of the newly opened petals has smaller base of near White 155A that quickly suffuses to a broad edging of near to between Red-Purple 60B to D and Red 53B. The bud does open up well and is not prevented from opening by wet, hot or dry weather.

BLOOM

When fully open, the bloom is moderately large for the class, ranging from 5 to 6 cm. in diameter. Petalage is double with 24 to 28 petals and 2 to 5 petaloids arranged regularly. When partially open, the bloom form is somewhat high centered to globular, and the petals are somewhat spiraled to cupped with petal edges slightly rolled outward. When fully open, the bloom form is somewhat more cupped to full, and the petals are more loosely cupped to undulated with petal edges moderately rolled outward.

PETALS

The petals are of moderately heavy substance and of medium thickness, with inside surface somewhat satiny to velvety and outside surfaces slightly shiny. The outside petals are very broadly obovate to nearly round in shape with apices somewhat rounded to flat and usually tipped with one tip. The inside petals are broadly obovate nearly round in shape with apices somewhat rounded and usually tipped with on tip.

NEWLY OPENED FLOWER

The following description is of color values observed in flowers on a plant grown outside in Upland, Calif. in the month of February. Colors may be modified by being washed or shaded or tinted with other colors.

The outside surface of the outer, intermediate and inner petals has a broad base of near White 155A that gradually suffuses to an edging of near to between Red-Purple 60C and Red 53B. The inside surface of the outer, intermediate and inner petals has a smaller base of near White 155A that quickly suffuses to a broad edging of near to between Red-Purple 60C to D and Red 53B.

The general color effect of the newly opened flower is near to between Red-Purple 60C to D and Red 53B with a eyezone of near White 155A.

THREE DAY OLD FLOWER

The outside surface of the outer and inner petals has a broad base of near White 155B that gradually suffuses to an edging of near to between Red-Purple 60D and Red 54A. The inside surface of the outer and inner petals has a broad base of near White 155B that gradually suffuses to a less broad edging of near to between Red-Purple 60D and Red 54A.

The general color effect of the three day old flower is near to between Red-Purple 60D and Red 54A with a broader eyezone of near White 155B.

On the spent bloom, the petals usually persist, fading to near White 155B with a fine edging of near to between Red 54D and Red-Purple 63C, and are not particularly affected by hot, wet or dry weather.

In February, blooms on the bush growing in the garden generally last from four to five or more days. Cut roses grown outdoor and kept at normal indoor living temperatures generally last from five or more days.

MALE REPRODUCTIVE ORGANS

Stamens are average to many in number and are arranged irregularly about the pistil; a few are mixed with petaloids. The filaments are of medium to long length, most with anthers. The anthers are medium size for the class and all open approximately at the same time. Anther color is near Yellow-Orange 22C when immature and near Greyed-Orange 164B at maturity. Pollen is moderate to abundant and near Yellow-Orange 20D in color.

FEMALE REPRODUCTIVE ORGANS

Pistils are somewhat above average in number (approximately 60). The styles are moderately uneven, moderately short to average in length, average in caliper, and somewhat loosely bunched. Stigma color is near Yellow 4D. Ovaries are usually all enclosed in the calyx.

Hips on this variety when grown in Upland, Calif. are of moderately short to average in length, somewhat globular in form, and near Red 42A in color when ripe. The hip surface is very smooth with moderately thick fleshy walls. The sepals fall quickly. Seeds are somewhat few to average in number (approximately 5 to 10), and moderately large in size for the class.

FOLIAGE

The compound leaves are usually comprised of three to five leaflets and are borne abundantly. The leaves are moderately large for the class (from 2.5 to 3.5 cm. in length), very heavy in texture, and very glossy in finish. The leaflets are shaped very oval with moderately acute apices and somewhat round to acute bases. Their margins are usually doubly serrate to irregular.

The upper surface of the mature leaf is near to between Green 139A and Green 136A. The under surface of the mature leaf is near to between Green 147C and Green 139C. The upper surface of the young leaf is near Green 139A, usually heavily suffused with near Greyed-Purple 183C. The under surface of the young leaf is near Green 139C, usually lightly suffused with near Greyed-Purple 184C.

The rachis is somewhat average to heavy in caliper and somewhat grooved with some stipitate gland on the edges of the upper side. The under side of the rachis is mostly smooth with one to three small prickles.

The stipules are moderately long with medium width with somewhat long straight points.

The plant displays an above average degree of resistance to powdery mildew and rust as compared to other commercial varieties grown under comparable conditions in Upland, Calif.

GROWTH

The plant is of a dwarf, bushy, upright medium height habit for the class with moderately full branching. It displays very vigorous growth and the canes somewhat medium to heavy caliper for the class. The ultimate plant height attained is substantially 18–24 inches, but can be maintained at lower heights by occasional selective pruning.

The major stems are near to between Yellow-Green 146C and Green 139C. They bear few large prickles which are somewhat medium length to long for the class. The large prickles are almost straight pointed slightly downward with a moderately long narrow base; prickle color is near Greyed-Orange 165A. The major stem bears no small prickles and no hairs.

The branches near to between Yellow-Green 146A and Green 139A. They bear several large prickles which are somewhat medium length to long for the class. The large prickles are almost straight pointing slightly downward with a moderately long narrow base; prickle color is near Greyed-Orange 164B. The branches bear no prickles and no hairs.

The new shoots are near Yellow-Green 146A often heavily suffused with near Greyed-Purple 184A. They bear several large prickles which are somewhat medium length to long for the class. The large prickles are almost straight pointed slightly downward with a moderately long narrow base; prickle color is near Greyed-Purple 185A. The shoots bear no small prickles and no hairs.

I claim:

1. A new and distinct variety of hybrid miniature rose plant, substantially as shown and described, characterized by large pointed buds and well-formed blooms, flower coloration of deep pink to red with a white eye-zone and reverse, long lasting flowers, abundant glossy foliage of good disease resistance, and a vigorous productive plant.

* * * * *

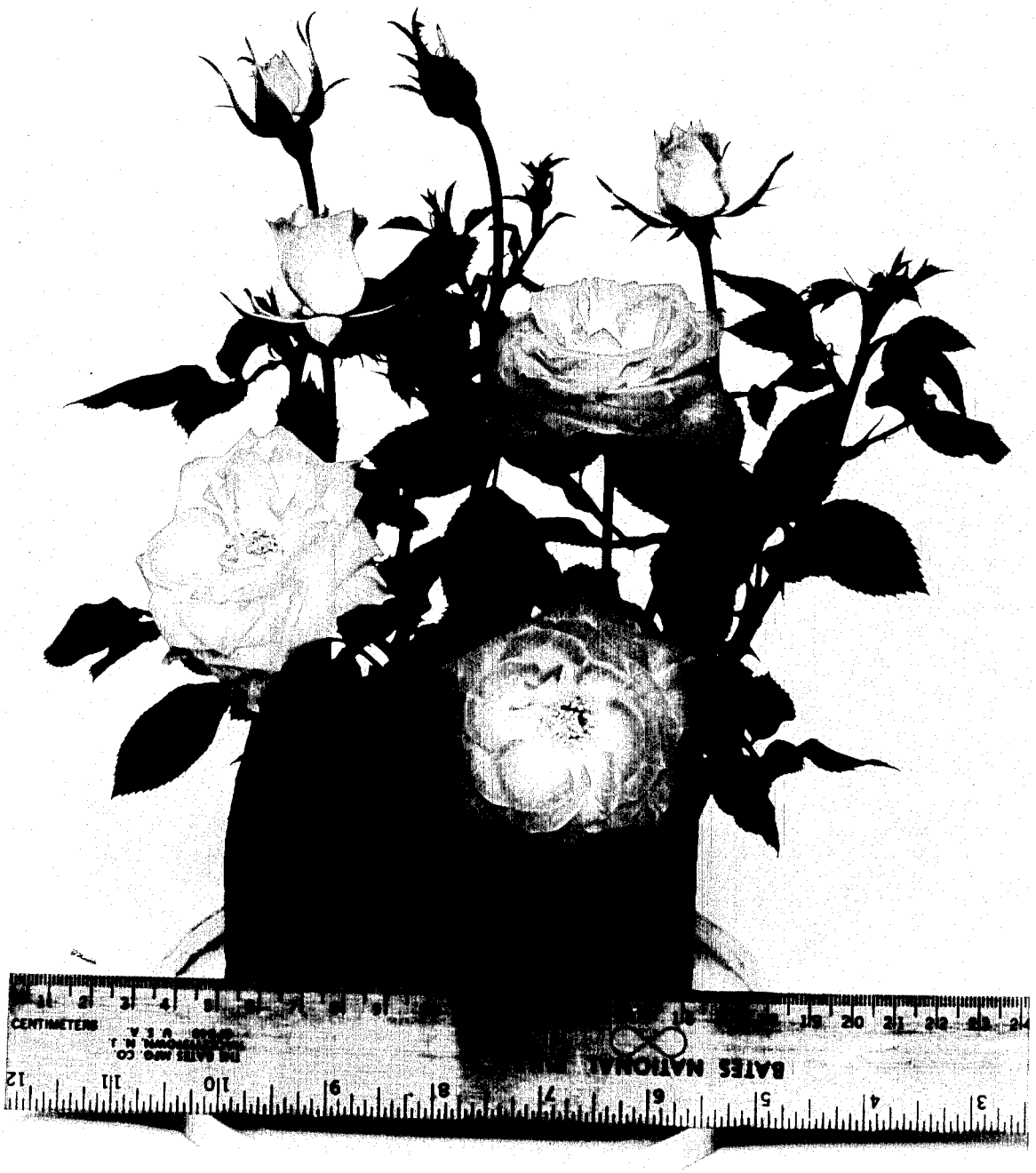
CENTIMETERS
BATES NATIONAL